(12) United States Patent
Lieberman (10) Patent No.: US 11,717,372 B2
(45) Date of Patent: Aug. 8, 2023

(54) SHAPE MEMORY SURGICAL SPONGE FOR RETRACTING THE DURA DURING A LAMINECTOMY PROCEDURE

(71) Applicant: Phoenix Spine Holdings, Inc., Phoenix, AZ (US)

(72) Inventor: Daniel Lieberman, Phoenix, AZ (US)

(73) Assignee: Phoenix Spine Holdings, Inc., Phoenix, AZ (US)

( * ) Notice: Subject to any disclaimer, the term of this patent is extended or adjusted under 35 U.S.C. 154(b) by 207 days.

(21) Appl. No.: 15/902,795

(22) Filed: Feb. 22, 2018

(65) Prior Publication Data

US 2019/0254768 A1 Aug. 22, 2019

(51) Int. Cl.

| A61B 90/00 | (2016.01) |
| A61B 18/20 | (2006.01) |
| A61F 13/36 | (2006.01) |
| A61B 17/00 | (2006.01) |
| A61B 17/16 | (2006.01) |

(Continued)

(52) U.S. Cl.
CPC ............ *A61B 90/03* (2016.02); *A61B 18/20* (2013.01); *A61B 90/04* (2016.02); *A61F 13/36* (2013.01); *A61B 17/1671* (2013.01); *A61B 2017/00867* (2013.01); *A61B 2017/0212* (2013.01); *A61B 2018/00339* (2013.01); *A61B 2018/00601* (2013.01); *A61B 2090/036* (2016.02); *A61B 2090/049* (2016.02); *A61B 2090/08021* (2016.02); *A61B 2217/007* (2013.01)

(58) Field of Classification Search
CPC ..... A61B 90/03; A61B 90/04; A61B 2090/031–049; A61B 2090/0801–08021; A61B 2017/0212; A61B 2017/0225; A61B 2017/00867; A61B 2017/00526; A61B 2017/0262; A61B 2018/00339; A61B 17/1671; A61B 17/3494; A61B 18/20; A61B 2018/00601; A61B 2090/036; A61B 2217/007; A61B 17/02; A61B 2217/005; A61F 2210/0014; A61F 2/4611; A61F 2/82–97; A61F 2/0045; A61F 2/0063; A61F 2002/4495; A61F 2002/4615; A61F 2002/821–9665; A61F 13/36

USPC ........................................................ 600/37

See application file for complete search history.

(56) References Cited

U.S. PATENT DOCUMENTS 4,844,065 A * 7/1989 Faulkner ................ A61B 17/30
606/107
5,569,183 A 10/1996 Kieturakis
(Continued)

OTHER PUBLICATIONS

European Search Report, EP Appl. No. EP 17803535.8, dated May 24, 2019, 10 pgs.
(Continued)

*Primary Examiner* — Sunita Reddy
(74) *Attorney, Agent, or Firm* — Jennings, Strouss & Salmon, P.L.C.

(57) ABSTRACT

Methods and apparatus for retracting the dura away from a cutting tool during a laminectomy procedure. The method includes inserting a memory shape surgical sponge (patty) into an initial epidural space between the dura and the tool used to decompress (e.g., drill) the lamina. As the lamina is further decompressed, the patty tends to spring back toward its nominal position, urging the dura away from the decompression and isolating the dura from the drill.

16 Claims, 5 Drawing Sheets

(51) Int. Cl.
    *A61B 18/00*     (2006.01)
    *A61B 17/02*     (2006.01)

(56) References Cited

U.S. PATENT DOCUMENTS

| | | |
|---|---|---|
| 6,127,597 A | 10/2000 | Beyar et al. |
| 2004/0024463 A1 | 2/2004 | Thomas, Jr. et al. |
| 2005/0187140 A1 | 8/2005 | Hunter et al. |
| 2005/0197661 A1* | 9/2005 | Carrison .......... A61B 17/32002 606/170 |
| 2006/0147492 A1 | 7/2006 | Hunter et al. |
| 2009/0318968 A1 | 12/2009 | Duggal et al. |
| 2010/0063590 A1 | 3/2010 | Cannestra |
| 2010/0081866 A1* | 4/2010 | Goddard ............... A61F 2/0045 600/37 |
| 2010/0087713 A1* | 4/2010 | Eliash .................. A61B 17/02 600/206 |
| 2010/0331883 A1* | 12/2010 | Schmitz ............. A61B 17/1659 606/249 |
| 2012/0016192 A1 | 1/2012 | Jansen et al. |
| 2017/0325852 A1 | 11/2017 | Chen et al. |

OTHER PUBLICATIONS

International Search Report; PCT/US19/19207 dated May 14, 2019, 2 pgs.
Written Opinion of International Search Report; PCT/US179/19207 dated May 14, 2019, 4pgs.

\* cited by examiner

SHAPE MEMORY SURGICAL SPONGE FOR RETRACTING THE DURA DURING A LAMINECTOMY PROCEDURE

TECHNICAL FIELD

The present invention relates, generally, to devices and methods for protecting the dura from cutting tools used in laminectomy procedures and, more particularly, to a shape retention surgical patty configured to retract the dura away from the lamina during decompression.

BACKGROUND

The lamina is a posterior arch of the vertebral bone lying between the spinous process and the transverse processes of each vertebra. Each pair of laminae, together with the spinous process disposed therebetween, make up the posterior wall of the bony spinal canal (vertebral foramen).

The dura mater (or simply "dura") refers to the outermost of the three layers of the meninges that surround the spinal cord and carry blood from the brain toward the heart. In the spine, the epidural space refers to the anatomic region between the outermost part of the spinal canal (formed by the surrounding vertebrae) and the dura mater (which encloses the arachnoid mater, subarachnoid space, the cerebrospinal fluid, and the spinal cord). In humans the epidural space contains lymphatics, spinal nerve roots, loose connective tissue, fatty tissue, small arteries, and a network of internal vertebral venous plexuses.

A laminectomy is a surgical procedure in which a portion of respective adjacent laminae is removed, for example, by drilling into the lamina. The back muscles are pushed aside rather than cut and the parts of the vertebra adjacent to the lamina are left intact.

A laminectomy procedure breaks the continuity of the rigid ring of the spinal canal to allow the soft tissues within the canal to: 1) expand (decompress); 2) change the contour of the vertebral column; or 3) permit access to deeper tissue inside the spinal canal. A laminectomy also contemplates a spinal operation that partially or wholly removes one or both lamina, as well as other posterior supporting structures of the vertebral column, including ligaments and additional bone. The actual bone removal—referred to as decompression—may be carried out with a variety of surgical tools, including drills, rongeurs and lasers. Removal of substantial amounts of bone and tissue may require additional subsequent procedures such as spinal fusion to stabilize the spine.

Laminectomies are commonly performed to treat spinal stenosis. Spinal stenosis is the single most common diagnosis that leads to spinal surgery, of which a laminectomy represents one component. The lamina of the vertebra is removed or trimmed to widen the spinal canal and create more space for the spinal nerves and thecal sac. Surgical treatment that includes a laminectomy is the most effective remedy for severe spinal stenosis.

Those skilled in the art will appreciate that it is important to avoid damaging the dura and surrounding epidural tissue while decompressing (e.g., drilling) the laminae.

Presently known laminectomy procedures typically employ a surgical patty comprising an absorbent material (e.g., cotton) to facilitate irrigation and removal of waste fluid from the site. Existing surgical pattys are disadvantageous, however, in that they do not adequately isolate the dura and surrounding tissue from the tools used to remove the lamina. Moreover, presently known pattys have no underlying structural architecture or spring action to expand the patty in the direction of the dura as the lamina is decompressed.

Methods and apparatus are thus needed which overcome the limitations of the prior art.

Various features and characteristics will also become apparent from the subsequent detailed description and the appended claims, taken in conjunction with the accompanying drawings and this background section.

BRIEF SUMMARY

Various embodiments of the present invention relate to a surgical patty comprising a shape memory alloy and an absorbent material for use in retracting the dura away from a cutting tool during a laminectomy procedure. In an exemplary method, the surgeon crimps the patty with forceps and slides it through a tube (typically 18 millimeter diameter) for insertion into the surgical site. As the portions of the lamina are cut or drilled away, the spring action of the patty urges it back to it's pre-crimped shape. As it expands, the patty fills the increasingly decompressed epidural space, while at the same time gently urging the dura away from the cutting tool.

In various embodiments, the patty be any desired shape, such as a thin rectangle in the range of ⅛ to ½ inch by ⅛ to 1 inch, and pre-formed to exhibit a curvature that approximates the curvature of the spinal canal, for example having a radius on the order of 0.1 to 10 centimeters, and preferably about 1.5 cm. The pre-formed patty may traverse an arc in the range of 90 to 270 degrees, and preferably about 150 degrees. Alternatively, the sponge may assume a conical or any other suitable planar or non-planar geometric shape which, when folded or crimped and inserted into the surgical site, expands into the epidural space between the dura and the inside surface of the spinal canal. As the surgeon decompresses the site by removing bone and ligaments, the patty tends to return to its nominal shape to fill the void created by decompression.

In an embodiment the patty may comprise a nitinol skeletal mesh with interwoven rayon, cotton, and/or other absorbent fibers. The sponge (patty) may be manufactured by: i) creating a wire mesh or screen using a shape memory material such as nitinol; ii) heating the mesh and configuring it into a desired shape (e.g., a 15 degree deviation from planarity); ii) weaving the cotton fibers into the curved mesh; and iv) placing the final pre-shaped sponge into a sterile package. Alternatively, the fibers may be interwoven with the structural matrix before pre-forming into a desired shape.

Alternatively, a sheet of absorbent fabric may be adhered (e.g., using a biocompatible glue) to a micro "chicken wire" nitinol mesh or, alternatively, weaving the cottonoid fibers throughout the wire structure. In a primary use case, the surgical patty is in the range of ½ inch wide and 1 inch long, with a nitinol mesh forming a 15 degree are along the short axis of the sponge (much like a partial cone or partial cylinder).

Shape memory alloys such as nitinol are generally well known in the context of biocompatible materials and medical devices; see mddionline.com/article/superelastic-nitinol-medical-devices. In addition, the Vostra Neurosorb surgical patty can be manually configured (i.e., without the use of nitinol or other shape retaining material) into a desired shape for various surgical applications; see medicalexpo.com/pdf/vostra/neurosorb/84939-160532.

It should be noted that the various inventions described herein, while illustrated in the context of a laminectomy procedure, are not so limited. Those skilled in the art will appreciate that the inventions described herein may contemplate any procedure in which it is desired to isolate tissue from a surgical tool.

Various other embodiments, aspects, and features are described in greater detail below.

BRIEF DESCRIPTION OF THE DRAWING FIGURES

Exemplary embodiments will hereinafter be described in conjunction with the following drawing figures, wherein like numerals denote like elements, and.

DETAILED DESCRIPTION OF PREFERRED EXEMPLARY EMBODIMENTS

The following detailed description of the invention is merely exemplary in nature and is not intended to limit the invention or the application and uses of the invention. Furthermore, there is no intention to be bound by any theory presented in the preceding background or the following detailed description.

Various embodiments of the present invention relate to devices and associated methods for performing surgical procedures, including but not limited to laminectomy procedures, in which a shape retention—or "stay-in-shape"—surgical sponge is placed between an anatomical structure to be protected (e.g., dura) and a surgical tool (e.g., drill).

By way of brief introduction, presently known laminectomy procedures typically use an absorbant sponge to facilitate irrigation and drainage. That is, the sponge helps distribute clean water to the site, as well as drawing blood and waste (e.g., bone and tissue fragments) away from the site. Presently known surgical sponges used for this purpose, however, lack an architectural framework capable of urging the dura away from the tool used to cut or drill the lamina, rendering the dura potentially vulnerable to inadvertent damage by the cutting tool.

To address this drawback, the present invention provides an armoured patty comprising an absorbant material integrated with or otherwise secured to a memory shape supporting structure, configured to expand into the epidural space which increases in size during decompression of the lamina. In doing so, the patty effectively isolates the dura from the tool used to cut the lamina, thereby protecting the dura from inadvertent damage.

In an embodiment, a guide sleeve is inserted through the patient's side to permit access to the disc region. After creating an initial void in the epidural space by removing a small piece of the lamina, the armoured patty is crimped upon itself and installed through the sleeve into the void. As the lamina is further decompressed, the surgeon adjusts the patty as needed (while maintaining a view of the epidural space through the tube) to maintain the patty between the surgical tool (e.g., drill) and the dura. As successive cutting operations continue to increase the size of the epidural space, the shape memory patty unfolds and expands into the space, urging the dura away from the tool, thereby protecting the dura from accidental nicking, cutting, or other damage.

In other embodiments, the patty may be made from flame resistant material, inasmuch as high speed drills may generate substantial heat when contacting the patty and surrounding tissue and bony material.

Figure 1:
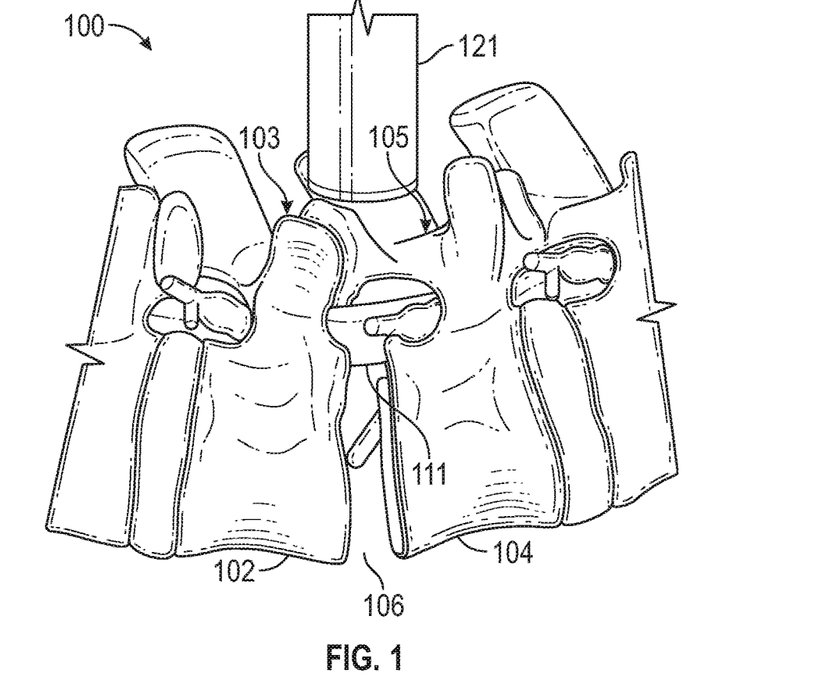
FIG. 1 is a schematic view of an exemplary surgical site including a first vertebral body, a second vertebral body, and a disc region disposed therebetween, where the disc material has been removed to prepare the site for a laminectomy in accordance with various embodiments.

Referring now to FIG. 1, a laminectomy surgical site 100 includes a first vertebral body 102 including a first lamina 103, a second vertebral body 104 including a second lamina 105, and a disc region 106 disposed therebetween, where the disc material has been removed, for example in preparation for a subsequent direct lateral interbody fusion (DLIF) surgical procedure. The dura in extends along the spinal canal from right to left in FIG. 1. An installation tube or other access device 121 may be provided to facilitate access to the site by various surgical tools, and/or through which the patty may be inserted.

Figure 2:
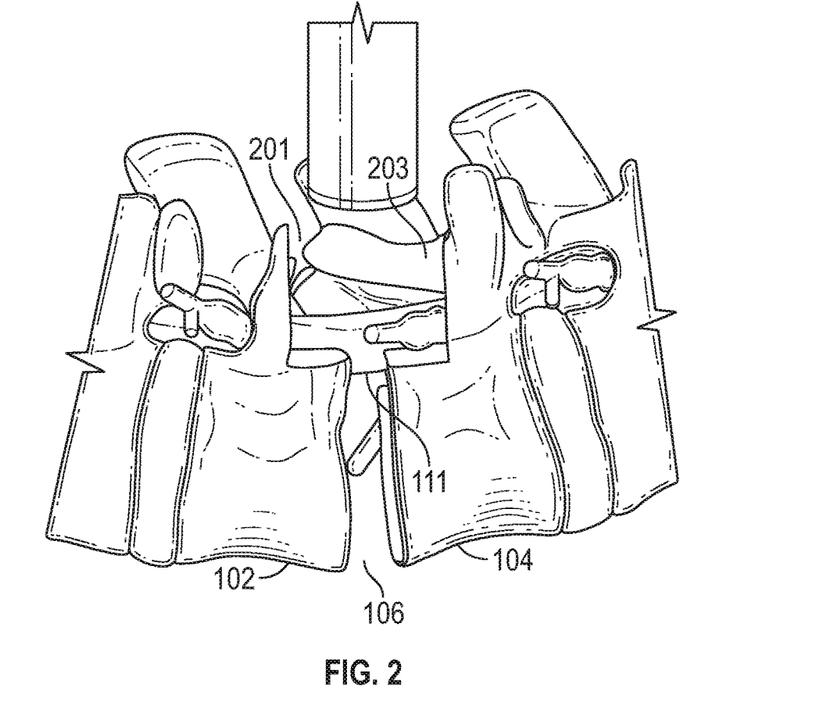
FIG. 2 is a schematic view of the site shown in FIG. 1 following the laminectomy, with portions of adjacent laminae removed in accordance with various embodiments.

FIG. 2 depicts the site of FIG. 1 following the partial removal of each lamina. In particular, first lamina 103 has been decompressed to create a first region 201, and second lamina 105 has been decompressed to create a second region 203; together, first and second regions 201, 203 comprise an expanded (decompressed) epidural space proximate the dura 111 in the vicinity of disc space 106. In this regard, the regions 201, 203 are schematically represented as being bounded by flat bony surfaces; however, those skilled in the art will appreciate that the actual anatomical surfaces may be non-planar.

Figure 3:
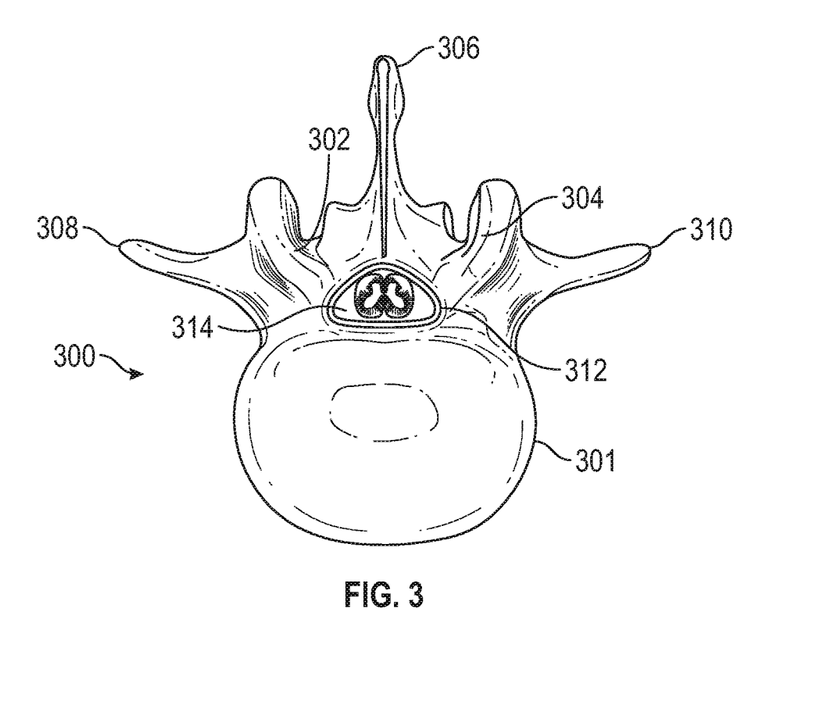
FIG. 3 is an axial view of an exemplary vertebral body depicting the dura within the spinal canal bounded by respective laminae in accordance with various embodiments.

FIG. 3 is an exemplary vertebra 300 including a vertebral body 301, respective laminae 302, 304, spinous process 306, respective transverse processes 308, 310, and spinal canal 312 enclosing the dura 314. The epidural space is the region between the inside of the spinal canal 312 and the outside of the dura 314.

Figure 4:
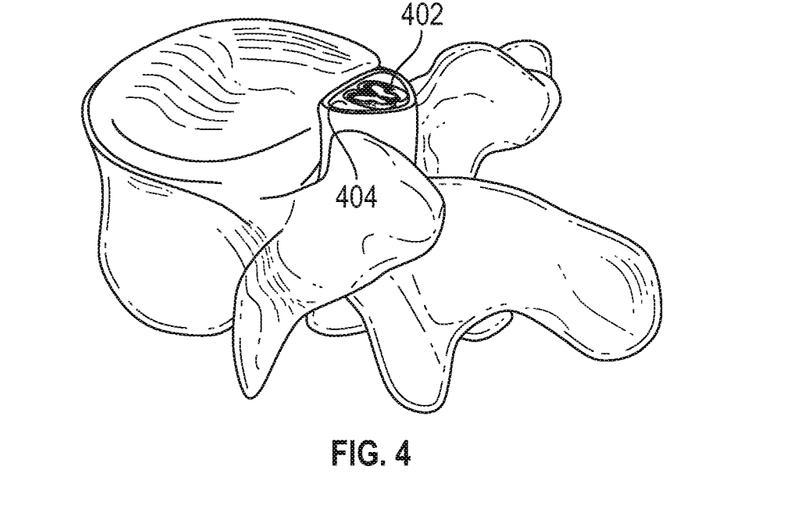
FIG. 4 is a top perspective view of the bony structure shown in FIG. 3 in accordance with various embodiments.

FIG. 4 is a perspective view of the vertebra shown in FIG. 3, and depicts the spinal cord 402 enclosed within the dura 404 which extends along the spinal canal.

An exemplary method of using the shape retention patty of the present invention in the context of a laminectomy will now be described in conjunction with FIGS. 5-8.

Figure 5:
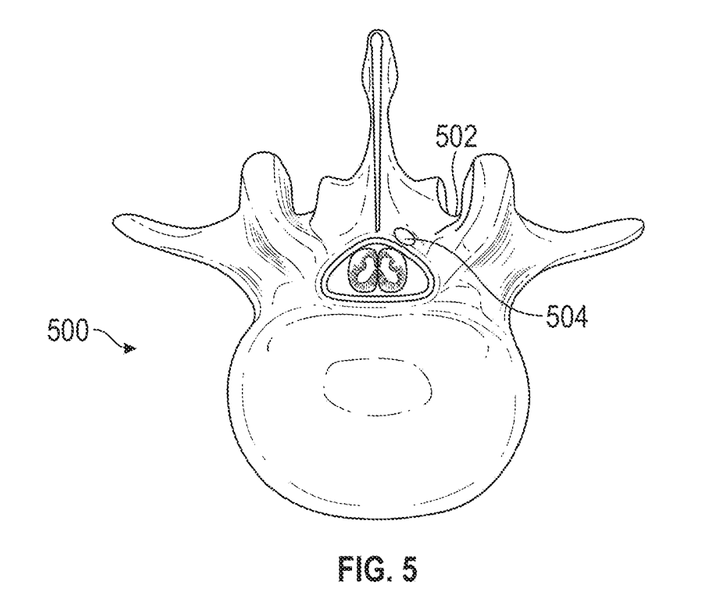
FIG. 5 is a schematic representation of an exemplary vertebra illustrating an initial expansion of the epidural space caused by removing a small portion of the lamina in accordance with various embodiments.

FIG. 5 is an exemplary vertebra 500 illustrating an initial expansion of the epidural space caused by removing a small portion of the lamina 502 to create a small cavity or recess 504. In this regard, those skilled in the art will appreciate that the epidural space may initially be too small to accommodate a patty without removing at least some portion of the lamina. Accordingly, drilling or otherwise cutting away a first portion of the lamina to create the cavity 504 provides an initial site for receiving the crimped patty, suitably installed through an access tube.

Figure 6:
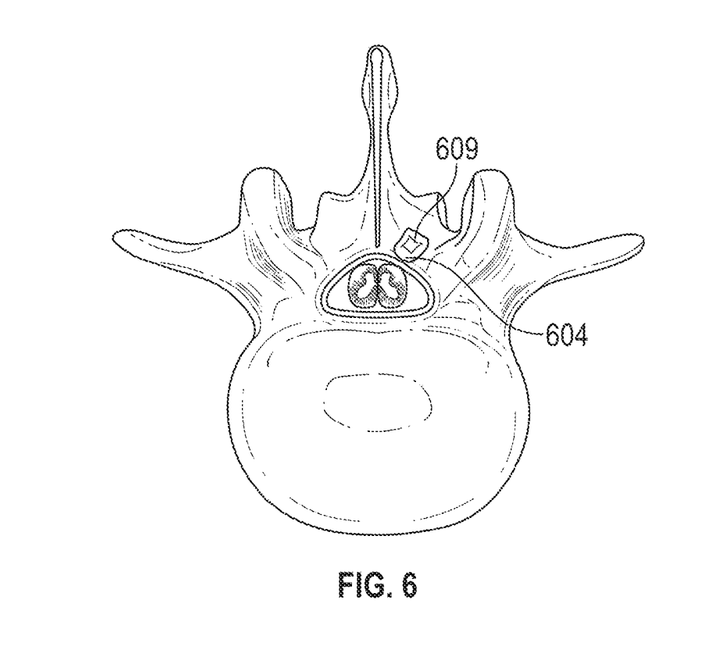
FIG. 6 is a schematic view of the vertebra of FIG. 5, showing a crimped patty placed into an increasing epidural space in accordance with various embodiments.

FIG. 6 depicts the vertebra of FIG. 5, showing a crimped patty 609 placed into an enlarged epidural space 604. As the surgeon removes additional lamina bone, the resulting epidural space increases, whereupon the patty "uncrimps" to fill the space, effectively urging the dura away from the tool used to cut the lamina.

Figure 7:
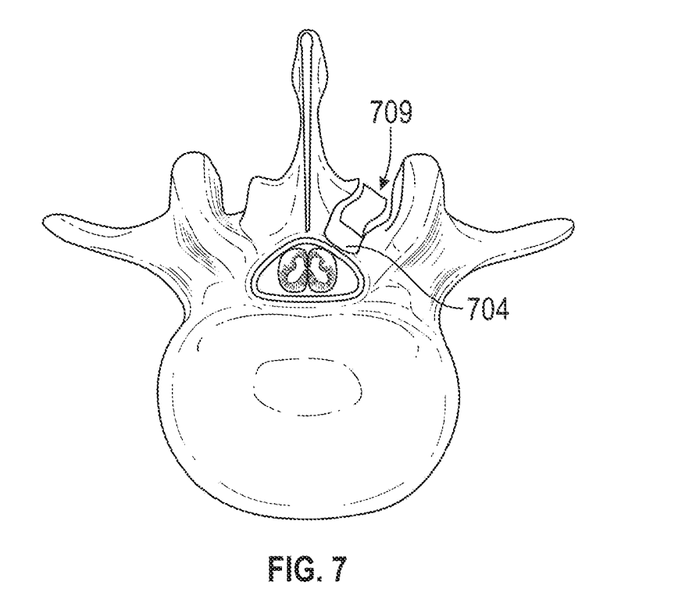
FIG. 7 is a schematic view of the vertebra of FIGS. 5 and 6, showing the patty expanding as the epidural space is decompressed in accordance with various embodiments.

Referring now to FIG. 7, the patty 709 tends to return to its original pre-formed shape, expanding into the progressively larger epidural space 704 as the space is further decompressed.

Figure 8:
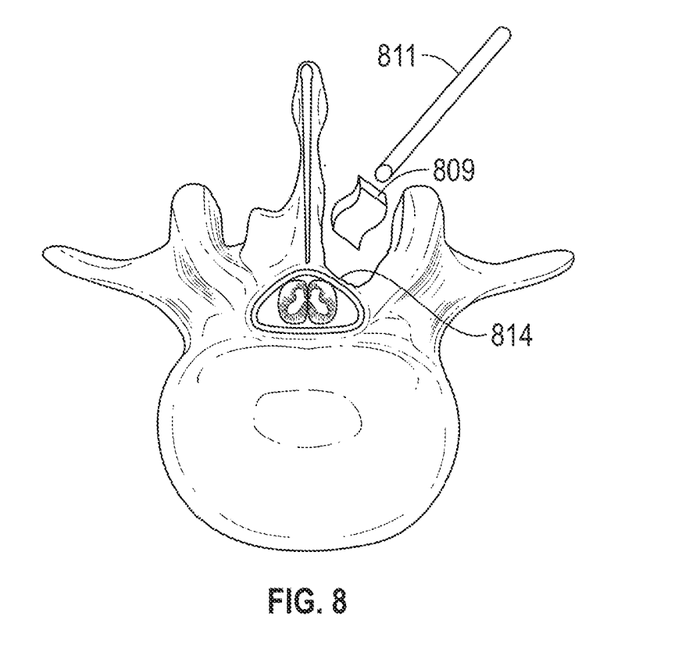
FIG. 8 is a schematic view of the vertebra of FIGS. 5-7, showing the expanding patty retracting the dura away from the cutting tool as the lamina is further decompressed in accordance with various embodiments.

FIG. 8 schematically illustrates the increasingly expanding patty 809 retracting the dura 814 away from the cutting tool 811 as the lamina is fully decompressed.

Figure 9:
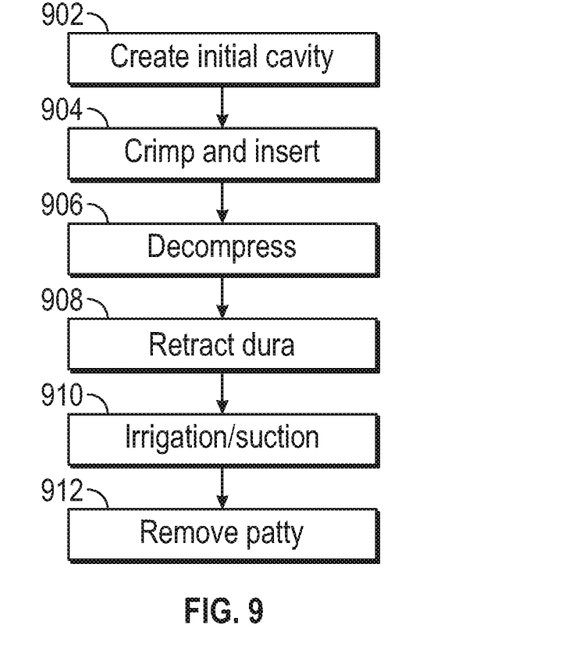
FIG. 9 is a flow chart illustrating an exemplary method of using the surgical patty in the context of a laminectomy procedure in accordance with various embodiments.

FIG. 9 is a flow chart illustrating an exemplary method 900 of using a shape retention surgical patty in the context of a laminectomy procedure. More particularly, the method includes: i) removing a small piece of lamina bone to create an initial epidural expansion cavity (Task 902); ii) crimping a shape retaining patty and inserting it into the cavity (Task 904), for example by sliding the patty through an installation tube; iii) successively cutting additional bony material from the lamina (Task 906); iv) adjusting the position of the patty so that it retracts the dura away from the cutting tool (Task 908); v) applying irrigation and suction to the surgical site proximate the patty during decompression (Task 910), using the patty to facilitate the transfer of irrigation fluid to the site and the removal of waste fluid from the site while protecting the dura; and vi) removing the patty upon completion of the laminectomy (Task 912).

Figure 10:
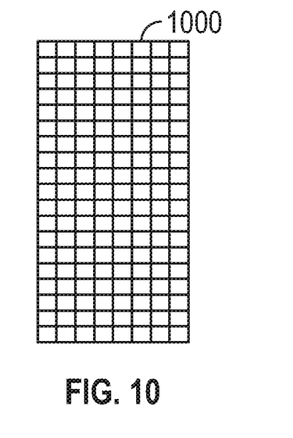
FIG. 10 is a schematic representation of an exemplary support structure for a memory shape patty in accordance with various embodiments.

FIG. 10 is a schematic representation of an exemplary support structure 1000 for a memory shape patty. The structure may comprise any suitable metallic, non-metallic, alloy (e.g., Nitinol), and/or other biocompatible material which may be: i) combined with absorbant sponge material; ii) pre-formed into a desired nominal shape; iii) crimped, folded, rolled, or otherwise manipulated into a smaller form factor to facilitate delivery into a small cavity at the surgical site; and iv) flare open under the intrinsic spring action of the support structure material to approach it's nominal pre-formed shape as the cavity size increases during decompression.

Figure 11:
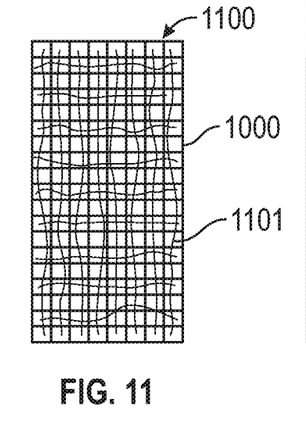
FIG. 11 is a schematic representation of the support structure of FIG. 10 including absorbant fibers or an absorbant layer interwoven into or otherwise adhered to the structure in accordance with various embodiments.

FIG. 11 is a schematic representation of a patty assembly 1100 including a support structure 1000 and absorbant fibers or an absorbant layer 1101 interwoven into or otherwise secured or adhered to the structure.

Figure 12:
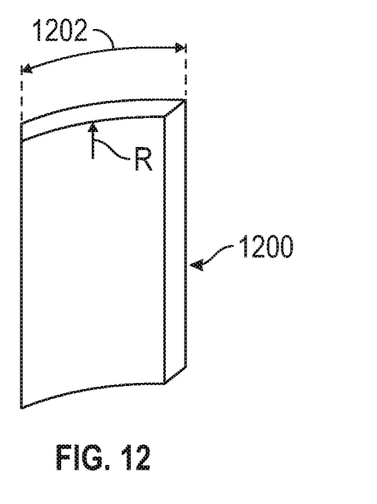
FIG. 12 is a schematic representation of the support structure of FIG. 11 shown after undergoing thermal, chemical, and/or mechanical treatment to pre-form the patty assembly into a desired nominal shape in accordance with various embodiments.

FIG. 12 is a schematic representation of a patty assembly 1200 generally analogous to that of FIG. 11, shown after undergoing thermal, chemical, and/or mechanical treatment to pre-form the patty assembly into a desired nominal shape. In various embodiments, the nominal shape of the patty may be tuned to the surgical environment. In the context of a laminectomy, the patty may exhibit a curvature which approximates the curvature of the inside of the spinal canal, for example having a radius R in the range of 0.05 to 10 centimeters, and preferably about 1 to 2 cm. The patty 1200 may be curved or twisted in two or three dimensions about one or plural axes. In the illustrated embodiment, the patty is curved along an arc 1202 in the range of 60 to 270 degrees, and preferably about 150 degrees.

A method is thus provided for isolating a dura structure from a cutting tool during a laminectomy procedure. The method includes: crimping a pre-formed memory shape patty; inserting the crimped patty into an installation tube; positioning a distal end of the installation tube proximate an epidural space between adjacent vertebrae; sliding the crimped patty along the installation tube; discharging the crimped patty from the distal end of the installation tube proximate the epidural space; removing a first portion of a lamina using the cutting tool; positioning the patty between the dura structure and the cutting tool; and thereafter removing a second portion of the lamina with the patty disposed between the dura structure and the cutting tool.

In an embodiment, the cutting tool comprises one of a drill, a rongeur and a laser.

In an embodiment, the pre-formed memory shape patty comprises a substantially rectangular sheet having a length dimension in the range of ⅛ to 1 inch, and a width dimension in the range of ⅛ to ½ inch.

In an embodiment, the method also includes manufacturing the pre-formed memory shape patty according to the following steps: creating a substantially planar wire mesh support structure using a shape memory material; heating the support structure to impart a curvature; and attaching absorbant fibers to the curved support structure.

In an embodiment, the pre-formed memory shape patty comprises nitinol.

In an embodiment, the pre-formed memory shape patty comprises a wire mesh support structure having absorbant fibers attached thereto.

In an embodiment, the absorbant fibers are adhered to a surface of the mesh support structure.

In an embodiment, the absorbant fibers are interwoven into the mesh support structure.

In an embodiment, crimping the pre-formed memory shape patty comprises folding the patty using forcepts.

In an embodiment, the installation tube is characterized by a cross sectional area in the range of 100 to 500 $mm^2$.

In an embodiment, the installation tube is characterized by a cross sectional area in the range of about 250 $mm^2$.

In an embodiment, the method also includes creating an initial epidural cavity proximate the vertebrae.

In an embodiment, positioning a distal end of the installation tube comprises positioning the distal end proximate the initial epidural cavity.

In an embodiment, discharging the crimped patty comprises discharging the patty into the initial epidural cavity.

In an embodiment, the method also includes: successively decompressing a volume surrounding the initial epidural cavity; and manipulating the patty between at least two successive decompression cycles to maintain the patty between the dura structure and the cutting tool.

In an embodiment, the method also includes: supplying irrigation fluid proximate the patty; and withdrawing drainage fluid proximate the patty.

A method is also provided for using a shape retention patty to protect a dura while performing a laminectomy. The method includes: creating an initial epidural cavity proximate a lamina; folding the patty and introducing the folded patty into the initial cavity; placing a cutting tool proximate the initial cavity; positioning the patty between the dura and the cutting tool; and decompressing the lamina while maintaining the patty between the cutting tool and the dura.

In an embodiment, the shape retention patty comprises a mesh support structure having interwoven absorbant fibers.

In an embodiment, the shape retention patty comprises a substantially rectangular sheet having a curved portion.

A surgical assembly is also provided for use in decompressing a lamina. The assembly includes: a tubular installation device; a patty including a shape retaining support structure and absorbant material; a crimping tool; and a cutting tool; wherein the crimping tool, the tubular installation device, and the patty are configured to facilitate crimping the patty and introducing the crimped patty proximate the lamina As used herein, the word "exemplary" means "serving as an example, instance, or illustration." Any implementation described herein as "exemplary" is not necessarily to be construed as preferred or advantageous over other implementations, nor is it intended to be construed as a model that must be literally duplicated.

While the foregoing detailed description will provide those skilled in the art with a convenient road map for implementing various embodiments of the invention, it should be appreciated that the particular embodiments described above are only examples, and are not intended to limit the scope, applicability, or configuration of the invention in any way. To the contrary, various changes may be made in the function and arrangement of elements described without departing from the scope of the invention.

The invention claimed is:

1. A method of isolating a dura structure from a cutting tool during a laminectomy procedure, the method comprising:
   crimping a pre-formed memory shape patty for retracting the dura structure away from the cutting tool during the laminectomy procedure, wherein the patty comprises a memory shape support structure material and an absorbent material secured to the memory shape support structure material;
   inserting the crimped patty into an installation tube;
   positioning a distal end of the installation tube in an interlaminar space proximate an epidural space between adjacent vertebrae;
   sliding the crimped patty along the installation tube in such a way that there remains a direct visual path through the tube to the epidural space;
   discharging the crimped patty from the distal end of the installation tube into the interlaminar space proximate the epidural space;
   removing a first portion of a lamina using the cutting tool;
   positioning the patty between the dura structure and the cutting tool; and
   thereafter removing a second portion of the lamina with the patty disposed between the dura structure and the cutting tool;
   wherein the positioning and discharging of the patty is accomplished by decompressing the lamina while maintaining the patty between the cutting tool and the dura structure during the laminectomy procedure; and
   wherein the patty unfolds and expands into the epidural space under the intrinsic spring action of the memory shape support structure material during the laminectomy procedure decompression as the resulting epidural space increases, to approach the patty's pre-formed shape, isolating and urging the dura structure away from the cutting tool.

2. The method of claim 1, wherein the cutting tool comprises one of a drill, a rongeur and a laser.

3. The method of claim 2, wherein the pre-formed memory shape patty comprises a substantially rectangular sheet having a length dimension in the range of ⅛ to 1 inch, and a width dimension in the range of ⅛ to ½ inch.

4. The method of claim 2, further comprising manufacturing the pre-formed memory shape patty according to the following steps:
   creating a substantially planar wire mesh support structure using a shape memory material;
   heating the support structure to impart a curvature; and
   attaching absorbent fibers to the curved support structure.

5. The method of claim 2, wherein the pre-formed memory shape patty comprises nitinol.

6. The method of claim 2, wherein the pre-formed memory shape patty comprises a wire mesh support structure having absorbent fibers attached thereto.

7. The method of claim 6, wherein the absorbent fibers are adhered to a surface of the mesh support structure.

8. The method of claim 6, wherein the absorbent fibers are interwoven into the mesh support structure.

9. The method of claim 6, wherein crimping the pre-formed memory shape patty comprises folding the patty using forceps.

10. The method of claim 2, wherein the installation tube is characterized by a cross sectional area in the range of 100 to 500 mm$^2$.

11. The method of claim 10, wherein the installation tube is characterized by a cross sectional area of about 250 mm$^2$.

12. The method of claim 1, wherein the step of removing a first portion of a lamina using the cutting tool creates an initial epidural cavity proximate the vertebrae.

13. The method of claim 12, wherein the step of positioning a distal end of the installation tube comprises positioning the distal end proximate the initial epidural cavity.

14. The method of claim 13, wherein the step of discharging the crimped patty comprises discharging the patty into the initial epidural cavity.

15. The method of claim 14, further comprising:
   successively decompressing a volume surrounding the initial epidural cavity; and
   manipulating the patty between at least two successive decompression cycles to maintain the patty between the dura structure and the cutting tool.

16. The method of claim 15, further comprising:
   supplying irrigation fluid proximate the patty; and
   withdrawing drainage fluid proximate the patty.

* * * * *